(12) United States Patent
Kwon et al.

(10) Patent No.: US 8,575,344 B2
(45) Date of Patent: Nov. 5, 2013

(54) PROCESS FOR PREPARING VORICONAZOLE BY USING NEW INTERMEDIATES

(75) Inventors: Hyuk Chul Kwon, Gyeonggi-Do (KR); Man Dong Rho, Seoul (KR); Kyung Hoi Cha, Gyeonggi-Do (KR)

(73) Assignee: Dongkook Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 13/577,055

(22) PCT Filed: Feb. 1, 2011

(86) PCT No.: PCT/KR2011/000689
§ 371 (c)(1),
(2), (4) Date: Aug. 3, 2012

(87) PCT Pub. No.: WO2011/096697
PCT Pub. Date: Aug. 11, 2011

(65) Prior Publication Data
US 2013/0005973 A1    Jan. 3, 2013

(30) Foreign Application Priority Data
Feb. 4, 2010    (KR) .................... 10-2010-0010467

(51) Int. Cl.
C07D 403/06    (2006.01)
(52) U.S. Cl.
USPC ........................................... 544/333; 544/242
(58) Field of Classification Search
USPC ................................................ 544/242, 333
See application file for complete search history.

(56) References Cited

U.S. PATENT DOCUMENTS 8,143,397 B2 * 3/2012 Benito et al. ................... 544/333
8,263,769 B2 * 9/2012 Moon et al. ................... 544/319

FOREIGN PATENT DOCUMENTS

| KR | 10-2009-0014468 A | 2/2009 |
| WO | 2007/013096 A1 | 2/2007 |
| WO | 2009-024214 A1 | 2/2009 |
| WO | 2009-084029 A2 | 7/2009 |

OTHER PUBLICATIONS

International Search Report dated Oct. 14, 2011 for PCT Application No. PCT/KR2011/000689.

* cited by examiner

*Primary Examiner* — Golam M M Shameem
(74) *Attorney, Agent, or Firm* — Edwards Wildman Palmer LLP

(57) ABSTRACT

Provided is a process for preparing Voriconazole represented by Chemical Formula 1. More particularly, the process for preparing Voriconazole of Chemical Formula 1 includes: carrying out the Reformatsky-type coupling reaction between a ketone derivative of Chemical Formula 4 and a pyrimidine derivative of Chemical Formula 5 to obtain a compound of Chemical Formula 3; reacting the substituents halo and oxysulfonyl with a hydrogen donor to obtain racemic Voriconazole of Chemical Formula 2; and carrying out optical isolation of the racemic Voriconazole by adding an adequate optically active acid thereto to obtain Voriconazole having high optical purity with high cost-efficiency and high yield.

[Chemical Formula 1]

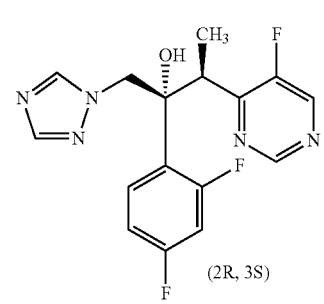

(2R, 3S)

8 Claims, No Drawings

PROCESS FOR PREPARING VORICONAZOLE BY USING NEW INTERMEDIATES

CROSS-REFERENCES TO RELATED APPLICATIONS

This application is a U.S. national phase application, pursuant to 35 U.S.C. §371, of PCT/KR2011/000689, filed Feb. 1, 2011, designating the United States and published in English on Aug. 11, 2011 as publication WO 2011/096697 A2, which claims priority to Korean Application No. 10-2010-0010467, filed Feb. 4, 2010. The entire contents of the aforementioned patent applications are incorporated herein by this reference.

TECHNICAL FIELD

The present invention relates to a novel process for preparing Voriconazole. More particularly, the present invention relates to a process for preparing Voriconazole represented by the following Chemical Formula 1, which includes: reacting a ketone derivative represented by the following Chemical Formula 4 with a novel pyrimidine derivative represented by the following Chemical Formula 5 to obtain a novel Voriconazole intermediate represented by the following Chemical Formula 3; removing the substituents effectively from the intermediate of Chemical Formula 3 to provide racemic Voriconazole represented by the following Chemical Formula 2; and adding an optically active acid thereto and carrying out crystallization to separate optical isomers.

[Chemical Formula 1]

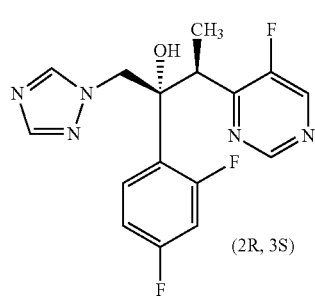

(2R, 3S)

[Chemical Formula 2]

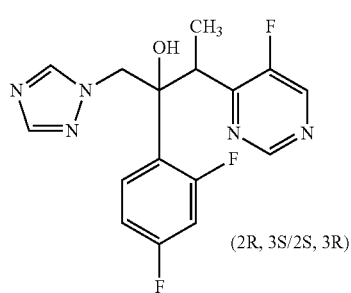

(2R, 3S/2S, 3R)

[Chemical Formula 3]

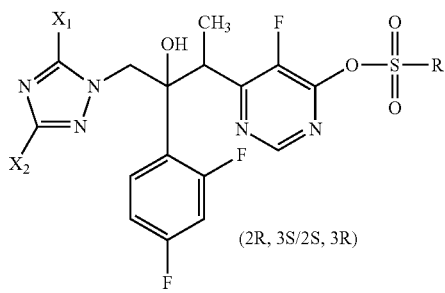

(2R, 3S/2S, 3R)

[Chemical Formula 4]

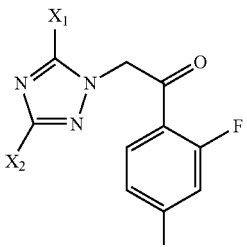

[Chemical Formula 5]

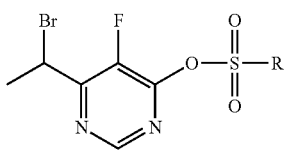

In the above Chemical Formulae 3-5, $X_1$ and $X_2$ independently represent H or halo; and R is $C_1$-$C_4$ alkyl or substituted or non-substituted phenyl, wherein the substituted phenyl may be substituted with at least one substituent selected from the group consisting of $C_1$-$C_4$ alkyl, alkoxy, halo, nitro and oxo.

BACKGROUND ART

Voriconazole is a second-generation triazole medication having a methyl group added to Fluconazole derivative, and provides fungicidal activity against *Aspergillus* infections or other filamentous fungal infections and a wide spectrum of anti-fungal activity. It is known that Voriconazole has a higher effect of treating invasive *Aspergillus* infections as compared to the existing Amphotericin, provides an excellent effect of treating infections caused by yeast fungi, and shows a stronger activity against fungal enzymes as compared to mammal enzymes by a factor of 250. In addition, Voriconazole has a higher binding ability to the demethylation step of 14-ranosterol in filamentous fungi than the corresponding binding ability in yeast fungi. Therefore, it shows fungicidal activity against some filamentous fungi but shows cytostatic activity against yeast fungi.

Voriconazole has an effect 60-100 times higher than Fluconazole against all *Candida* species including Fluconazole-resistant fungi. In the case of *Aspergillus*, Voriconazole is effective to all species including *Aspergillus terreus* that is resistant against Amphotericin. Referring to the structure of Voriconazole, it specifically has two adjacent asymmetric carbon atoms. Organic synthetic processes for producing such asymmetric carbon skeletons are limited significantly and have several problems in their industrial application. Moreover, known processes produce four types of stereoisomers during the synthesis due to the presence of the two asymmetric carbon atoms, resulting in a drop in yield during the separation of such isomers. Therefore, it is necessary to increase the stereoselectivity of the reaction in which the two asymmetric carbon atoms are formed and to realize effective separation of a desired stereoisomer in order to prepare Voriconazole more effectively.

In the synthesis of Voriconazole, it is thought that two important steps are step i) of preparing the pyrimidine derivative as an intermediate for use in the subsequent coupling reaction with high yield and high purity, and step ii) of increasing stereoselectivity in carrying out the coupling reaction between the pyrimidine derivative and the ketone derivative to obtain the resultant tertiary alcohol with high purity and high yield.

First, the pyrimidine derivative has been prepared as depicted in the following Reaction Scheme 1 under reflux without any solvent according to Korean Patent No. 1993-0011039 and EP 0440372. It is reported that the yield of pyrimidine derivative is as low as 66%. However, the method of Reaction Scheme 1 is not suitable for mass production owing to its severe reaction condition and low yield.

In addition, Korean Patent No. 10-0269048 and EP 0871625 disclose that the pyrimidine derivative is prepared via the method of Reaction Scheme 1 in the presence of a solvent, and the yield of the target product is 90%. However, in this case, there are problems in that phosphoryl chloride used in an excessive amount is hardly removed and the resultant product has low purity.

[Reaction Scheme 1]

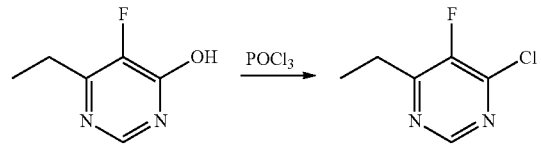

Meanwhile, Korean Unexamined Patent Publication No. 10-2009-0014468 discloses a process for preparing substituted thiopyrimidine derivatives by introducing a thiol group to a pyrimidine derivative, as shown in the following Reaction Scheme 2, to increase the purity of the pyrimidine derivative.

[Reaction Scheme 2]

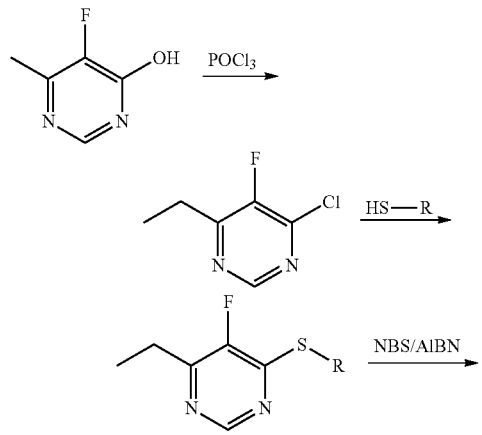

-continued

However, the above process is not amenable to industrial mass production due to the increased number of steps as compared to Reaction Scheme 1, the use of expensive thiol derivatives, and the bad odor generated during the step using thiol.

Next, Korean Patent No. 1993-0011039 and EP 0440372 disclose processes for carrying out a coupling reaction between pyrimidine derivatives and ketone derivatives. Herein, as shown in the following Reaction Scheme 3, LDA (lithium diisopropylamide), a strong base, or sodium bis(trimethylsilyl)amide is used to perform the coupling reaction.

[Reaction Scheme 3]

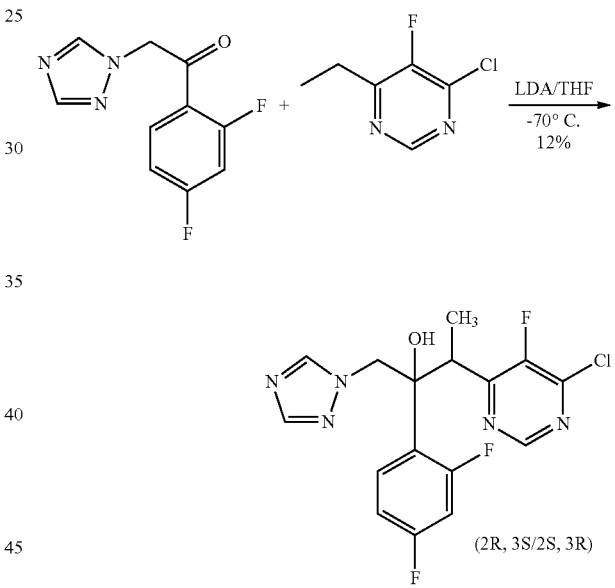

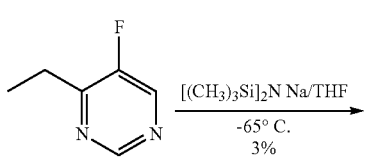

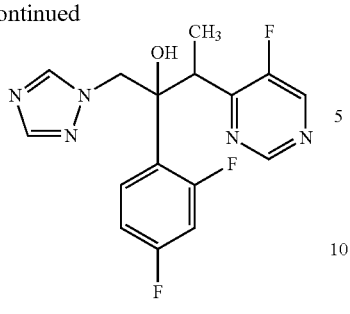

(2R, 3S/2S, 3R)

However, the above methods are problematic in that they use highly explosive strong bases and require equipment capable of cryogenic reaction. Above all, the methods provide very low yield due to the low stereoselectivity and difficulty in separating isomers, and thus are not amenable to mass production.

To overcome the above-mentioned problems, Korean Patent No. 10-0269048 and EP 0871625 disclose a method by which the stereoselectivity is increased through the Reformatsky-type coupling reaction as depicted in the following Reaction Scheme 4, and enantiomeric pairs (2R,3S/2S,3R) are separated in the form of their hydrochloride salts via crystallization, thereby increasing the yield.

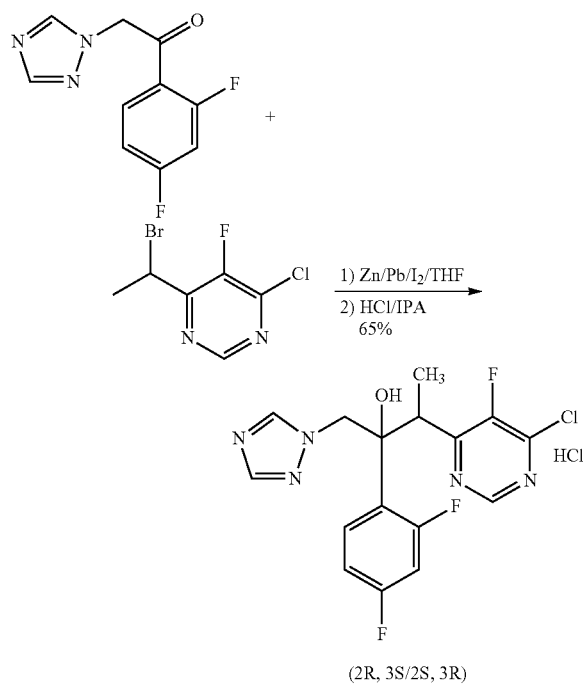

[Reaction Scheme 4]

(2R, 3S/2S, 3R)

However, the method is problematic in that it results in a relatively low yield of 65% despite a high ratio of the enantiomeric pairs of 9:1 (2R,3S/2S,3R:2R,3R/2S,3S). The method has another problem related to the removal of halo after the hydrochloride salts are treated with base.

EP 0069442 discloses a method for preparing 1-(2,4-difluorophenyl)-2-(1H-1,2,4-triazol-1-yl)ethanone, one of the main intermediates of Voriconazole, according to the following Reaction Scheme 5.

[Reaction Scheme 5]

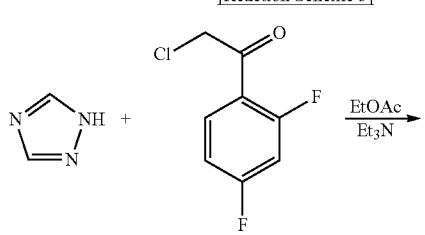

However, the above method provides a low yield of 40%. Under these circumstances, the present inventors have conducted intensive studies to develop a process for preparing Voriconazole, which includes forming a novel pyrimidine derivative as an intermediate with high purity and high yield, carrying out the Reformatsky-type coupling reaction between the intermediate and ketone derivative to increase the stereoselectivity, and carrying out crystallization to obtain Voriconazole with high purity and high yield in a large scale. The process for preparing Voriconazole using the novel intermediate is highly economical and efficient, and provides high yield and high purity.

SUMMARY OF THE DISCLOSURE

An object of the present invention is to provide a process for preparing Voriconazole of Chemical Formula 1, which includes preparing a novel pyrimidine derivative of Chemical Formula 5 having a sulfonate group introduced thereto with high yield through an efficient reaction path, and carrying out the Reformatsky-type coupling reaction between the pyrimidine derivative and a novel ketone derivative of Chemical Formula 4 to obtain a tertiary alcohol with high optical activity and high yield suitable for mass production.

In one general aspect, there is provided a process for preparing Voriconazole of the following Chemical Formula 1, the process including:

1) carrying out the Reformatsky-type coupling reaction between a compound of the following Chemical Formula 4 and a compound of the following Chemical Formula 5 to obtain a compound of the following Chemical Formula 3;

2) removing the substituents $X_1$, $X_2$ and $OSO_2R$ from the compound of Chemical Formula 3 to obtain race racemic Voriconazole of the following Chemical Formula 2, with the proviso that $X_1$ and $X_2$ are not removed when they both represent H; and 3) separating the isomers of the compound of Chemical Formula 2 with an optically active acid:

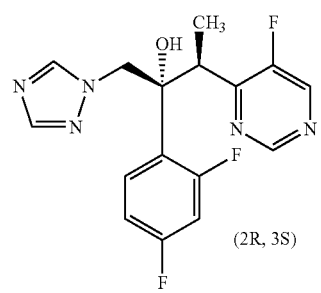

[Chemical Formula 1]

(2R, 3S)

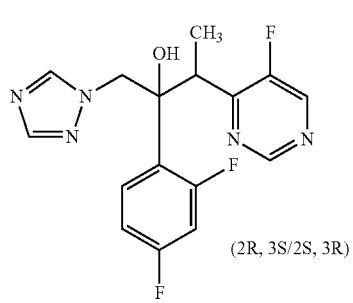

[Chemical Formula 2]

(2R, 3S/2S, 3R)

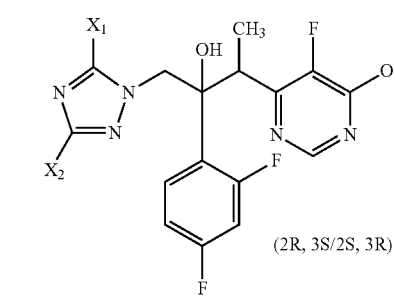

[Chemical Formula 3]

(2R, 3S/2S, 3R)

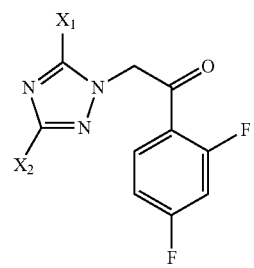

[Chemical Formula 4]

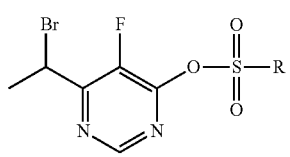

[Chemical Formula 5]

wherein $X_1$ and $X_2$ independently represent H or halo; and

R is $C_1$-$C_4$ alkyl or substituted or non-substituted phenyl, wherein the substituted phenyl may be substituted with at least one substituent selected from the group consisting of $C_1$-$C_4$ alkyl, alkoxy, halo, nitro and oxo.

According to an embodiment of the process for preparing Voriconazole of Chemical Formula 1, the Reformatsky-type-coupling reaction in step 1) is carried out at a temperature ranging from −15° C. to 0° C.

According to another embodiment of the process for preparing Voriconazole of Chemical Formula 1, step 2) is carried out by using Pd/C, Raney nickel or zinc as a catalyst. Herein, Pd/C is used in an amount of 2-30 wt % based on the amount of the compound of Chemical Formula 3.

According to still another embodiment of the process for preparing Voriconazole of Chemical Formula 1, step 2) is carried out by using hydrogen or ammonium formate as a hydrogen donor.

According to still another embodiment of the process for preparing Voriconazole of Chemical Formula 1, step 2) is carried out by using toluene, benzene, xylene or a mixture containing two or more of them as a reaction solvent.

According to yet another embodiment of the process for preparing Voriconazole of Chemical Formula 1, the compound of Chemical Formula 4 is obtained by reacting a compound represented by the following Chemical Formula 6 with a compound represented by the following Chemical Formula 7 under basic conditions:

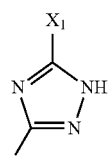

[Chemical Formula 6]

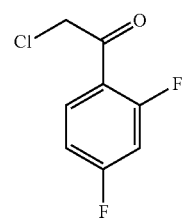

[Chemical Formula 7]

wherein $X_1$ and $X_2$ independently represent H or halo.

In the process for preparing Voriconazole according to the present invention, it is preferred that $X_1$ and $X_2$ independently represent halo, bromine being more preferred.

In another general aspect, there is provided a compound represented by the following Chemical Formula 5:

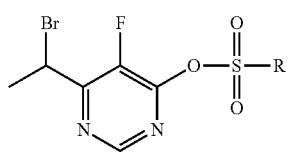

[Chemical Formula 5]

wherein R is $C_1$-$C_4$ alkyl or substituted or non-substituted phenyl, wherein the substituted phenyl may be substituted with at least one substituent selected from the group consisting of $C_1$-$C_4$ alkyl, alkoxy, halo, nitro and oxo. Preferably, R is $C_1$-$C_4$ alkyl. Preferably, the compound of Chemical Formula 5 is 6-(1-bromoethyl)-5-fluoropyrimidin-4-yl methanesulfonate.

In still another general aspect, there is provided a compound represented by the following Chemical Formula 3:

[Chemical Formula 3]

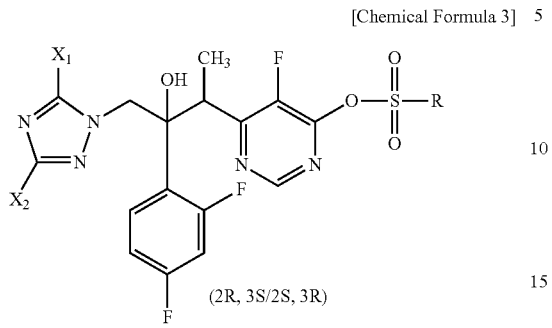

(2R, 3S/2S, 3R)

wherein $X_1$ and $X_2$ independently represent H or halo; and

R is $C_1$-$C_4$ alkyl or substituted or non-substituted phenyl, wherein the substituted phenyl may be substituted with at least one substituent selected from the group consisting of $C_1$-$C_4$ alkyl, alkoxy, halo, nitro and oxo. Preferably, R is $C_1$-$C_4$ alkyl. Preferably, the compound of Chemical Formula 3 is 6-[(2R,3S/2S,3R)-4-(3,5-dibromo-1H-1,2,4-triazol-1-yl)-3-(2,4-difluorophenyl)-3-hydroxybutan-2-yl]-5-fluoro-pyrimidin-4-yl methanesulfonate.

According to the present invention, it is possible to prepare the compound of Chemical Formula 3 with high purity and high yield through the effective preparation of the novel intermediate compounds of Chemical Formula 4 and Chemical Formula 5 used for synthesis of Voriconazole, followed by the Reformatsky-type coupling reaction between the compound of Chemical Formula 4 and the compound of Chemical Formula 5. Then, it is possible to obtain Voriconazole having high purity and high yield in a large scale by removing the substituents present on the triazole and pyrimidine structures in the resultant tertiary alcohol compound, and by carrying out optical isolation with an optically active acid.

DETAILED DESCRIPTION

Hereinafter, the embodiments of the present invention will be described in detail. According to some embodiments of the present invention, the novel intermediates can be obtained via the following Reaction Schemes 6 and 7. Finally, Voriconazole can be obtained according to the following Reaction Scheme 8.

[Reaction Scheme 6]

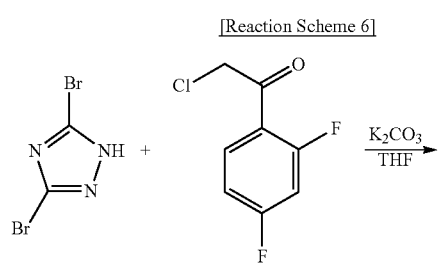

-continued

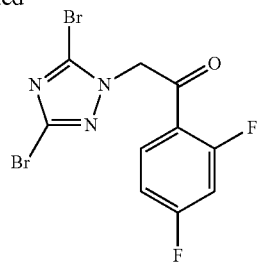

According to Reaction Scheme 6, 3,5-dibromo-1H-1,2,4-triazole is used as a starting material to obtain a novel intermediate with a purity of at least 99% with a yield of at least 85%, while minimizing generation of impurities. In addition, it is possible to facilitate crystallization after the Reformatsky-type coupling reaction so that the enantiomeric pairs (2R,3S/2S,3R) may be separated with ease from each other. In this manner, it is possible to increase the purity and the yield at the same time.

However, the scope of the present invention is not limited to the structures depicted in Reaction Scheme 6. For example, triazole substituted with a halogen atom other than bromine may also be used.

[Reaction Scheme 7]

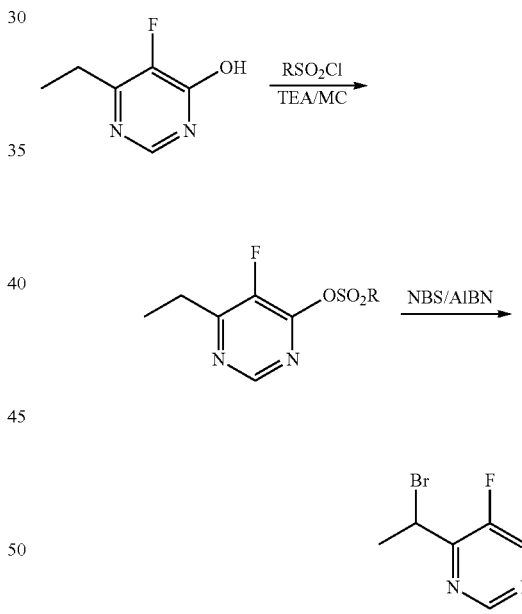

One important factor in the synthesis of Voriconazole is to prepare the pyrimidine derivative, which is another main intermediate used for the Reformatsky-type coupling reaction, with high purity and high yield. In this context, the methods according to the related art have problems in that $POCl_3$ used in an excessive amount is hardly removed, and the resultant product has a low purity of 80% or less. To solve such problems, as shown in Reaction Scheme 7, the substituted sulfonyl chloride is used in an amount of 1.1 equivalents under economical and mild reaction conditions. In this manner, it is possible to obtain a compound of Chemical Formula 5 with a purity of at least 90% and an overall yield of at least 97%, while minimizing generation of impurities.

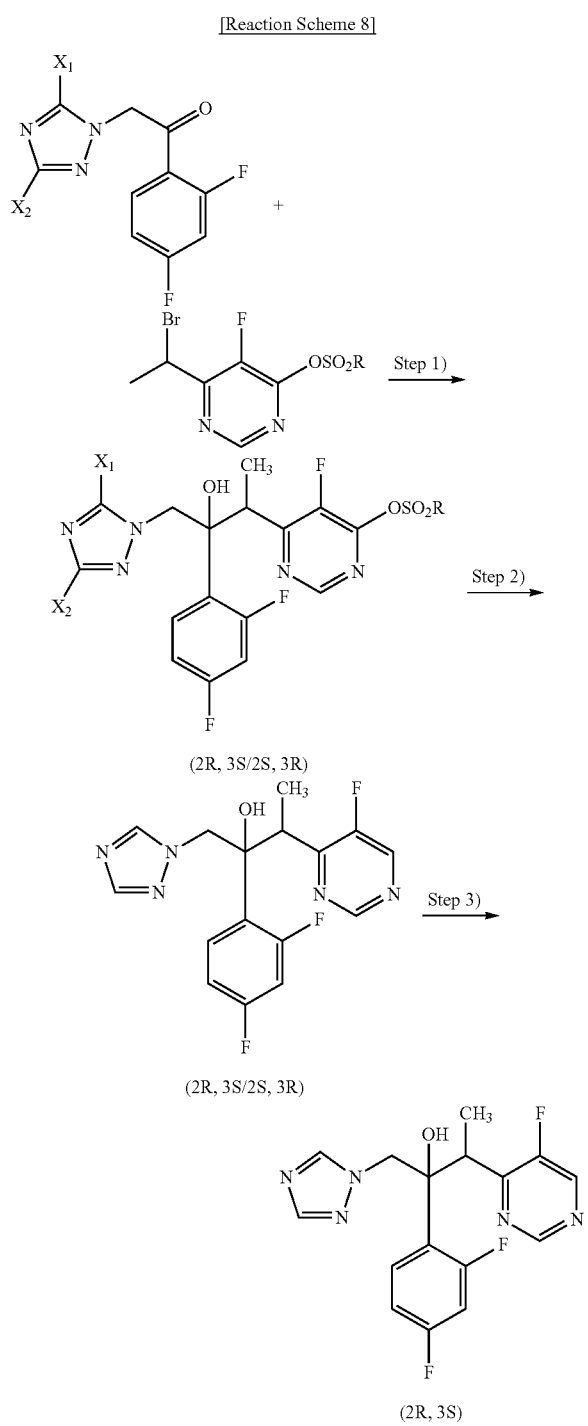

[Reaction Scheme 8]

As shown in Reaction Scheme 8, in step 1), the novel compounds represented by Chemical Formulae 4 and 5 (R=Me) are subjected to the Reformatsky-type coupling reaction to provide a compound of Chemical Formula 3 having a tertiary alcohol group.

In this case, the enantiomeric pairs produced from the Reformatsky-type coupling reaction exist in a ratio of 10:1 (2R,3S/2S,3R:2R,3R/2S,3S), and thus are separated with ease via crystallization in an organic solvent. In this manner, it is possible to obtain a compound of Chemical Formula 3 with a purity of at least 99% with a high yield of at least 75%.

In addition, step 2) includes preparing racemic Voriconazole of Chemical Formula 2 in the presence of a palladium catalyst by using hydrogen gas or ammonium formate as a hydrogen donor. The above reaction produces little impurities. Therefore, it is possible to obtain racemic Voriconazole of Chemical Formula 2 with a purity of at least 99% at a yield of at least 90%.

Step 3) includes reacting the compound of Chemical Formula 2 with an adequate optically active acid to obtain Voriconazole represented by Chemical Formula 1. Preferably, previously known R-(−)-10-camphor sulfonic acid is used as the optically active acid.

According to the above-described process, it is possible to obtain Voriconazole with a purity of at least 99.95% and high yield.

EXAMPLES

Examples will now be described. The following examples and experiments are for illustrative purposes only and not intended to limit the scope of the present invention.

Example 1

Preparation of 2-(3,5-dibromo-1H-1,2,4-triazol-1-yl)-1-(2,4-difluorophenyl)ethan-1-one First, 43.7 g of 3,5-dibromo-1H-1,2,4-triazole is introduced into 200 mL of tetrahydrofuran (THF), the resultant mixture is agitated, and 40.4 g of 2-chloro-2,4-difluoroacetophenone is further introduced thereto. Next, 36.3 g of potassium carbonate is introduced to the reaction mixture and the resultant mixture is agitated for 7 hours at room temperature. After the completion of the reaction, the reaction mixture is filtered, washed with 100 mL of tetrahydrofuran (THF), and concentrated at room temperature. Then, 437 mL of purified water is introduced so that the crystals are slurried, followed by filtering. The filtered crystals are reslurried in 175 mL of isopropanol and filtered again. The crystals are washed with 44 mL of isopropanol and dried with hot air at 50° C. to obtain 63.8 g of the title compound as a white solid (yield 87%, purity 99.2%, HPLC, detected at a wavelength of 256 nm, 18C 4.6×250 mm, mobile phase 60% ACN, flow rate 1 mL/min).

$^1$H-NMR (200 MHz, CDCl$_3$) δ (ppm): 8.11~8.03(1H), 7.11-6.96(2H), 5.51(2H).

Example 2

Preparation of 6-ethyl-4-fluoropyrimidin-4-yl methanesulfonate

First, 100 g of 6-ethyl-5-fluoropyrimidin-4-ol is introduced to 1000 mL of methylene chloride (MC), followed by agitation. Next, 196 mL of triethyl amine is introduced thereto at room temperature and 59.9 mL of methanesulfonyl chloride is added dropwise thereto. After the reaction mixture is agitated for 5 hours at room temperature, the reaction mixture is cooled to 5° C. and 126.75 g of acetic acid is introduced thereto. The reaction mixture is washed twice with 1000 mL of purified water, and then the organic layer is dried over magnesium sulfate, filtered and concentrated under reduced pressure to obtain 153.4 g of the title compound (yield 99%, purity 93.5%, HPLC, detected at a wavelength of 256 nm, 18C 4.6×250 mm, mobile phase 60% ACN, flow rate 1 mL/min).

$^1$H-NMR (200 MHz, CDCl$_3$) δ (ppm): 8.67(1H), 3.60(3H), 2.97-2.89(2H), 1.35(3H).

Example 3

Preparation of 6-(1-bromoethyl)-5-fluoropyrimidin-4-yl methanesulfonate

First, 153.4 g of 6-ethyl-4-fluoropyrimidin-4-yl methanesulfonate is dissolved into 100 mL of methylene chloride (MC), followed by agitation. Next, 186 g of N-bromosuccinimide (NBS) and 5.7 g of azobisisobutyronitrile (AIBN) are introduced thereto at room temperature. The reaction mixture is warmed to 45-50° C. and agitated for 12 hours. After the completion of the reaction, 1000 mL of purified water is introduced to the reaction mixture, followed by washing. Then, 66.2 g of sodium metabisulfite is introduced to and dissolved completely in 1000 mL of purified water to provide a solution, which, in turn, is introduced to the reaction mixture for washing. After that, 1000 mL of 5% sodium bicarbonate is introduced and the reaction mixture is washed. Then, the organic layer is dried over magnesium sulfate, filtered and concentrated under reduced pressure to obtain 218.3 g of the title compound (yield 104.7%, purity 93.1%, HPLC, detected at a wavelength of 256 nm, 18C 4.6×250 mm, mobile phase 60% ACN, flow rate 1 mL/min).

$^1$H-NMR (200 MHz, CDCl$_3$) δ (ppm): 8.75(1H), 5.42~5.35(1H), 3.60(3H), 2.07(3H).

Example 4

Preparation of 6-[(2R,3S/2S,3R)-4-(3,5-dibromo-1H-1,2,4-triazol-1-yl)-3-(2,4-difluorophenyl)-3-hydroxybutan-2-yl]-5-fluoropyrimidin-4-yl methanesulfonate Under nitrogen atmosphere, 68.7 g of zinc powder is introduced to 300 mL of dry tetrahydrofuran (THF), followed by agitation. Next, 5.4 g of lead powder is introduced thereto. At room temperature, 33.3 g of iodine is introduced and the resultant mixture is agitated for 1 hour. The reaction mixture is cooled to −15° C. In a separate container, 100 g of 2-(3,5-dibromo-1H-1,2,4-triazol-1-yl)-1-(2,4-difluorophenyl) ethan-1-one and 102.1 g of 6-(1-bromoethyl)-5-fluoropyrimidin-4-yl methanesulfonate are dissolved into 700 mL of tetrahydrofuran (THF) at room temperature, and the resultant solution is added dropwise to the reaction mixture for 1 hour. The resultant mixture is further agitated for 1 hour at −10° C. After the completion of the reaction, 500 mL of purified water is introduced and the reaction mixture is further agitated for 1 hour at room temperature. The solid residue is filtered through a Celite pad, followed by washing with 2000 mL of methylene chloride (MC). The filtered organic layer is washed with 1000 mL of 1N HCl and further washed with 1000 mL of saline. The organic layer is dried over magnesium sulfate, filtered and concentrated under reduced pressure. Then, 600 mL of ethyl acetate (EA) is introduced thereto and dissolved completely by heating. After that, 1800 mL of n-hexane is further introduced thereto and 50 mg of seeds are introduced while the mixture is agitated at 60° C. Once crystals are formed, 1200 mL of n-hexane is further introduced, and then the mixture is cooled gradually and filtered at room temperature. The resultant product is dried with hot air at 50° C. to obtain 118.5 g of the title compound as a white solid (yield 75.1%, purity 99.2%, HPLC, detected at a wavelength of 256 nm, 18C 4.6×250 mm, mobile phase 60% ACN, flow rate 1 mL/min).

$^1$H-NMR (200 MHz, CDCl$_3$) δ (ppm): 8.68(1H), 7.72~7.64(1H), 6.96-6.83(2H), 6.42(1H) 4.57(1H), 4.35(1H), 4.25(1H), 3.65(3H), 1.11(3H).

Example 5

Preparation of (2R,3S/2S,3R)-2-(2,4-difluoro phenyl)-3-(5-fluoropyrimidin-4-yl)-1-(1H-1,2,4-triazol-1-yl) butan-2-ol (racemic Voriconazole)

First, 100 g of 6-[(2R,3S/2S,3R)-4-(3,5-dibromo-1H-1,2,4-triazol-1-yl)-3-(2,4-difluorophenyl)-3-hydroxybutan-2-yl]-5-fluoropyrimidin-4-yl methanesulfonate is introduced to 1000 mL of toluene, followed by agitation. Next, 30 g of Pd/C (50% wet) and 105 g of ammonium formate are introduced, and the reaction mixture is warmed to 80° C. and agitated for 3 hours. After the completion of the reaction, the reaction mixture is cooled to room temperature and 1000 mL of purified water is introduced thereto, followed by filtering. The resultant product is washed with 500 mL of toluene to perform layer separation and further washed with 1000 mL of toluene. The organic layer is dried over magnesium sulfate, filtered and concentrated under reduced pressure. Then, 500 mL of isopropyl ether is introduced, and the mixture is warmed to 70° C., agitated for 1 hour, and further agitated at 5° C. for 1 hour, followed by filtering. The resultant product is dried with hot air at 50° C. to obtain 53.7 g of the title compound as a white solid (yield 92.5%, purity 99.5%, HPLC, detected at a wavelength of 256 nm, 18C 4.6×250 mm, mobile phase ACN:MeOH:H$_2$O=1:1:2, flow rate rte 1.5 mL/min).

$^1$H-NMR (200 MHz, CDCl$_3$) δ (ppm): 8.93(1H), 8.62(1H), 7.96(1 H), 7.61-7.57(1H), 7.55(1H), 6.87-6.80(2H), 6.47(1H), 4.73(1H), 4.32(1H), 4.14(1H), 1.11(3H).

Example 6

Isolation of Optical Isomers Preparation of (2R,3S)-2-(2,4-difluorophenyl)-3-(5-fluoropyrimidin-4-yl)-1-(1H-1,2,4-triazol-1-yl)butan-2-ol (R)-camsylate First, 10 g of (2R,3S/2S,3R)-2-(2,4-difluorophenyl)-3-(5-fluoropyrimidin-4-yl)-1-(1H-1,2,4-triazol-1-yl)butan-2-ol obtained from Example 5 is dissolved into 225 mL of acetone. Next, 13.3 g of R-(−)-10-camphorsulfonic acid dissolved in 75 mL of methanol is added thereto. The reaction mixture is refluxed for 1 hour and cooled gradually to room temperature to perform crystallization. Once crystals are precipitated, the reaction mixture is further agitated for 12 hours, filtered, washed with 10 mL of acetone, and dried with hot air for 12 hours at 50° C. to obtain 6.7 g of the title compound as a white solid (yield 40%, optical purity 99.9% or higher).

Example 7

Preparation of (2R,3S)-2-(2,4-difluorophenyl)-3-(5-fluoropyrimidin-4-yl)-1-(1H-1,2,4-triazol-1-yl)butan-2-ol (Voriconazole)

In 500 mL of dichloromethane, 50 g of (2R,3S)-2-(2,4-difluorophenyl)-3-(5-fluoropyrimidin-4-yl)-1-(1H-1,2,4-triazol-1-yl)butan-2-ol (R)-camsylate obtained from Example 6 is dissolved, and 500 mL of saturated sodium bicarbonate is introduced thereto, followed by agitation for 30 minutes. The organic layer is separated, and washed with 500 mL of saturated sodium bicarbonate and then with 500 mL of purified water. The organic layer is dried over magnesium sulfate, filtered, and concentrated under reduced pressure. The resultant product is subjected to crystallization using 50 mL of isopropanol and 250 mL of isopropyl ether, agitated for 2 hours at 5° C., and then filtered.

The resultant product is dried under reduced pressure for 12 hours at 50° C. to obtain 11.1 g of the title compound as a white solid (yield 92%, purity 99.95% or higher).

$^1$H-NMR (200 MHz, CDCl$_3$) δ (ppm): 8.93(1H), 8.62(1H), 7.96(1H), 7.61-7.57(1H), 7.55(1H), 6.87-6.80(2H), 6.47(1H), 4.73(1H), 4.32(1H), 4.14(1H), 1.11(3H).

The results of the above Examples 1-7 are summarized in the following Table 1.

TABLE 1

|  | Yield (%) | Purity (%) |
|---|---|---|
| Example 1 | 87 | 99.2 |
| Example 2 | 99 | 93.5 |
| Example 3 | 104.7 | 93.1 |
| Example 4 | 75.1 | 99.2 |
| Example 5 | 92.5 | 99.5 |
| Example 6 | 40 | 99.9 |
| Example 7 | 92 | 99.95 |

Comparative Example 1

Under nitrogen atmosphere, 9.35 g of zinc powder and 0.47 g of lead are introduced to 53 mL of dry tetrahydrofuran (THF) and the mixture is agitated for 3 hours under reflux. The reaction mixture is cooled to 25° C. and agitated continuously for 16 hours. In a separate container, 7.42 g of iodine is dissolved into 21 mL of dry tetrahydrofuran (THF) and the resultant solution is added dropwise to the reaction mixture over 80 minutes. Next, the reaction mixture is warmed to 45° C. and then cooled to 0° C.

At room temperature, 6.53 g of 1-(2,4-difluorophenyl)-2-(1H-1,2,4-triazol-1-yl)ethanone and 7.01 g of 6-(1-bromo ethyl)-4-chloro-5-fluoropyrimidine are dissolved into 53 mL of tetrahydrofuran (THF) and the resultant solution is added dropwise gradually to the reaction mixture, while maintaining the reaction temperature at 5° C. or lower. The reaction mixture is warmed to 25° C. and 8.84 g of glacial acetic acid dissolved in 84 mL of purified water is added dropwise to the reaction mixture. The solid metal residue is removed by filtering, the solvent is distilled off under reduced pressure, and the reaction product is extracted twice with 84 mL of ethyl acetate (EA). The extract is washed with 3.22 g of disodium ethylenediamine tetraacetate dihydrate dissolved in 161 mL of purified water, and further washed with 30 mL of saline. The organic layer is concentrated to a final volume of 56 mL, and a solution containing 1.2 g of hydrochloric acid in 6 mL of isopropanol is added dropwise thereto at 25° C. The resultant crystals are filtered, washed with 5 mL of EA, and dried under reduced pressure for 12 hours at 50° C. to obtain 5.99 g of the target compound (yield 48.7%, purity 96.2%, HPLC, detected at a wavelength of 256 nm, 18C 4.6×250 mm, mobile phase 60% ACN, flow rate 1 mL/min).

$^1$H-NMR (200 MHz, DMSO-d6) δ (ppm): 8.85(1H), 8.731H), 7.93(1H), 7.28~7.16(2H), 6.95~6.89(1H), 5.83(1H), 4.81(1H), 4.54(1H), 3.92(1H), 1.13(3H).

The results of Comparative Example 1 are summarized in the following Table 2.

TABLE 2

|  | Yield (%) | Purity (%) |
|---|---|---|
| Example 4 | 75.1 | 99.2 |
| Comparative Example 1 | 48.7 | 96.2 |

The invention claimed is:

1. A process for preparing Voriconazole of the following Chemical Formula 1, comprising the steps of:

1) carrying out the Reformatsky-type coupling reaction between a compound of the following Chemical Formula 4 and a compound of the following Chemical Formula 5 to obtain a compound of the following Chemical Formula 3;

2) removing the substituents $X_1$, $X_2$ and $OSO_2R$ from the compound of Chemical Formula 3 to obtain racemic Voriconazole of the following Chemical Formula 2, with the proviso that $X_1$ and $X_2$ are not removed when they both represent H; and 3) separating the isomers of the compound of Chemical Formula 2 with an optically active acid:

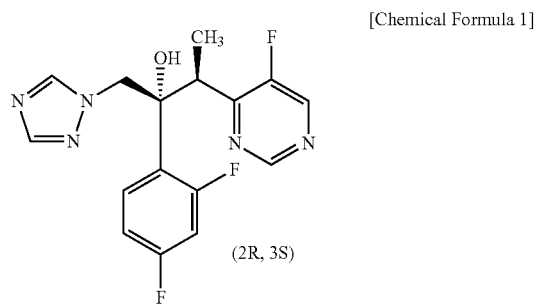 [SMILES: C[C@@H](c1ncncc1F)[C@](O)(Cn1cncn1)c1ccc(F)cc1F]

[Chemical Formula 1]

(2R, 3S)

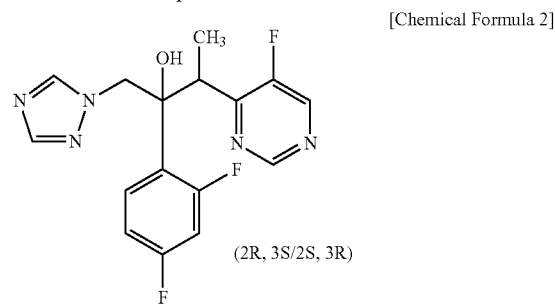

[Chemical Formula 2]

(2R, 3S/2S, 3R)

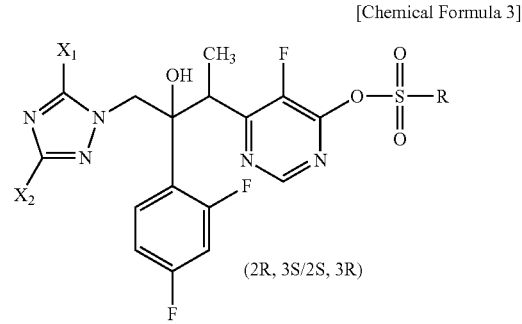

[Chemical Formula 3]

(2R, 3S/2S, 3R)

-continued

[Chemical Formula 4]

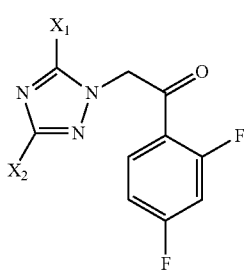

[Chemical Formula 5]

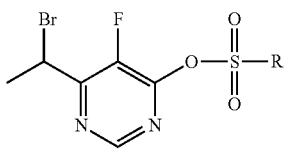

wherein $X_1$ and $X_2$ independently represent H or halo; and

R is $C_1$-$C_4$alkyl or substituted or non-substituted phenyl, wherein the substituted phenyl may be substituted with at least one substituent selected from the group consisting of $C_1$-$C_4$ alkyl, alkoxy, halo, nitro and oxo.

2. The process according to claim 1, wherein the Reformatsky-type coupling reaction in step 1) is carried out at a temperature ranging from −15° C. to 0° C.

3. The process according to claim 1, wherein step 2) is carried out by using Pd/C, Raney nickel or zinc as a catalyst.

4. The process according to claim 3, wherein Pd/C is used in an amount of 2-30 wt % based on the amount of the compound of Chemical Formula 3.

5. The process according to claim 1, wherein step 2) is carried out by using hydrogen or ammonium formate as a hydrogen donor.

6. The process according to claim 1, wherein step 2) is carried out by using toluene, benzene, xylene or a mixture containing two or more of them as a reaction solvent.

7. The process according to claim 1, wherein the compound of Chemical Formula 4 is obtained by reacting a compound represented by the following Chemical Formula 6 with a compound represented by the following Chemical Formula 7 under basic conditions:

[Chemical Formula 6]

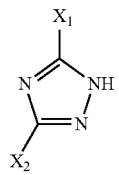

[Chemical Formula 7]

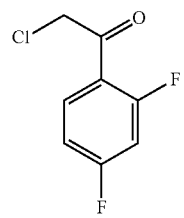

wherein $X_1$ and $X_2$ independently represent H or halo.

8. The process according to any one of claims 1 to 7, wherein $X_1$ and $X_2$ independently represent bromine.

* * * * *